(12) United States Patent
Swanson

(10) Patent No.: US 10,288,477 B2
(45) Date of Patent: May 14, 2019

(54) OPTICAL SYSTEMS WITH ASYMETRIC MAGNIFICATION

(71) Applicant: Rand Swanson, Bozeman, MT (US)

(72) Inventor: Rand Swanson, Bozeman, MT (US)

(*) Notice: Subject to any disclaimer, the term of this patent is extended or adjusted under 35 U.S.C. 154(b) by 270 days.

(21) Appl. No.: 15/255,385

(22) Filed: Sep. 2, 2016

(65) Prior Publication Data
US 2018/0066987 A1 Mar. 8, 2018

(51) Int. Cl.
G02B 13/08 (2006.01)
G01J 3/02 (2006.01)
G02B 27/30 (2006.01)
G01J 3/28 (2006.01)
G01J 3/06 (2006.01)

(52) U.S. Cl.
CPC .............. G01J 3/0205 (2013.01); G01J 3/06 (2013.01); G01J 3/2823 (2013.01); G02B 13/08 (2013.01); G02B 27/30 (2013.01); G01J 2003/2826 (2013.01)

(58) Field of Classification Search
CPC ................................ G02B 27/30; G02B 13/08
See application file for complete search history.

(56) References Cited

U.S. PATENT DOCUMENTS

| 1,962,892 | A | 6/1934 | Chretien |
|---|---|---|---|
| 2,017,634 | A | 10/1935 | Newcomer |
| 2,702,493 | A | 2/1955 | Knowlton |
| 2,720,813 | A | 10/1955 | Cox |
| 2,731,883 | A | 1/1956 | Kohler et al. |
| 2,780,141 | A | 2/1957 | Lubozhez |
| 2,821,110 | A | 1/1958 | Cook |
| 2,932,236 | A | 4/1960 | Delano |
| 2,933,017 | A | 4/1960 | Kingslake et al. |
| 2,956,475 | A | 10/1960 | Harris et al. |
| 3,517,984 | A | 6/1970 | Lindstedt et al. |
| 3,682,533 | A | 8/1972 | Vetter |
| 6,282,031 | B1 * | 8/2001 | Maruyama ............... G02B 5/04 359/669 |
| 6,310,731 | B1 | 10/2001 | Wartman et al. |
| 6,512,636 | B2 | 1/2003 | Schauss |
| 7,199,877 | B2 | 4/2007 | Kehoe |
| 8,384,896 | B2 | 2/2013 | Meade et al. |

* cited by examiner

Primary Examiner — Joseph P Martinez

(57) ABSTRACT

Optical systems are provided. In an embodiment, the optical system includes a first anamorphic optic having a first focal length and a first focal line, where the first focal line is parallel to a cross track direction. A second anamorphic optic has a second focal length and a second focal line, where the second focal length is different than the first first focal length. The second anamorphic optic is positioned such that the first focal line and the second focal line are in about the same location. The first and second anamorphic optics are aligned along an optical signal path, and are configured to provide afocal magnification to a signal beam along an along track direction to produce a magnified beam. A line scan imager includes an objective lens and a linear detector, and the second anamorphic optic is configured to direct the magnified beam at the objective lens.

20 Claims, 4 Drawing Sheets

OPTICAL SYSTEMS WITH ASYMETRIC MAGNIFICATION

TECHNICAL FIELD

The present disclosure generally relates to optical systems with asymmetric magnification, and more particularly relates to optical systems with asymmetric magnification intended for use with line scan imagers.

BACKGROUND

Line-scan imagers can be used for a wide range of applications. These range from remote sensing from satellites or airplanes for precision agriculture, to imaging products on a conveyor belt for sorting or quality control, to imaging on a microscope for biomedical research. The imagery collected by a line-scan imager is used to identify an object, feature, or characteristic within the imaged region, which typically requires analysis of the image. Once the object, feature, or characteristic is determined, the information may be used, for example, to locate regions in need of fertilizer in crop fields, determine which items should be removed from a conveyor belt, or help determine biological response to a drug.

A line scan imager accepts light or other electromagnetic radiation and directs that light toward a detector. The detector typically includes a plurality of sensors arranged in a linear manner, where the detector produces an electrical signal based on the type and/or intensity of electromagnetic radiation that impinges on the sensors of the detector. A line scan imager is typically associated with images that correspond to long, thin rectangles, thus approximating a line. This image corresponds to the linear nature of the detector, so the line scan imager may be configured to "see" one long, thin rectangular region, typically called a "line," across the width of the object imaged by the line-scan imager. The line scan imager can then take multiple readings as the object being imaged moves (or conversely, the line-scan imager moves), so each section of the region of interest is successively monitored by the line scan imager as the object of interest moves relative to the line-scan imager. Putting together the imaged "lines" sequentially provides an image of the region of interest. The line scan image, which typically includes a plurality of lines, can then be analyzed to identify objects, features, or characteristics within the region imaged by the line-scan imager. Light or other electromagnetic radiation sources may be directed at the region imaged by the line-scan imager, where the light may be reflected, transmitted, or emitted by items present in the imaged region. For example, one type of plastic may reflect a different intensity of electro-magnetic radiation at a particular frequency as compared to other types of plastic, such that the different types of plastics can be identified by the line scan imager. The information gathered by the line scan imager can then be transferred to an actuator that automatically sorts the different types of plastics or other items. Line scan imagers have many other uses, such as monitoring of geographic areas from a flying vehicle. Illumination may also be provided naturally, such as by the sun.

The line scan imager typically requires a certain magnitude of light or other signal to accurately detect and identify different items, similar to the human eye needing a certain amount of light to see and identify different items. The electrical signal produced by a sensor of the detector is generally proportional to several influencing factors, including: the radiance magnitude of the incoming light or electromagnetic radiation; the amount of time the light contacts the detector to produce the electrical signal; the sensor area; the efficiency of the sensor; and the spectral bandwidth of the incoming light incident on the sensor. Many line scan imagers include an aperture to limit the incoming light to a desired area, and the size of this aperture influences the electrical signal magnitude.

Often there is a desire to increase the line-scan frequency. For example, smaller objects may become of interest, thus requiring improved resolution, which in turn requires higher line-scan frequencies. Alternatively, there may be an economic incentive to increase the speed of a conveyor belt with items that are imaged by a line-scan imager, and thus the line-scan imager needs to image at a higher frequency. As the line-scan frequency increases, the amount of time for the sensor to produce an electrical signal decreases, and this lowers the electrical signal produced by the sensor. In some cases, the radiance can be increased by shining a brighter light or other electromagnetic source on the region of interest to increase the radiance. However, as the intensity of the electromagnetic radiation source increases, the amount of power required for that electromagnetic radiation source also increases. In some cases, the intensity of the electromagnetic radiation source is so high that the items of interest can be damaged, such as if the motion of a conveyor belt stops while the electromagnetic radiation source is operating. For example, the light source can be so intense it thermally damages (burns or cooks) the items on a conveyor belt if the conveyor belt stops, such as for mechanical reasons. Optical systems may be used to focus or otherwise manipulate the light or electromagnetic radiation before entry into the line scan imager, and these optical systems can improve operations in various manners. For example, a filter may remove light frequencies that interfere with the identification of certain items.

Accordingly, it is desirable to provide optical systems that improve the efficiency of line scan imagers. Furthermore, it is desirable to provide optical systems that will not degrade, or may even improve, the spatial resolution of line scan imagers. That is, it is desirable for line scan imagers to resolve smaller objects in their field of view than traditional line scan imagers, and an optical system that improves the efficiency of the line scan imager should not degrade its ability to resolve small objects. Other desirable features and characteristics of the present embodiment will become apparent from the subsequent detailed description and the appended claims, taken in conjunction with the accompanying drawings and this background of the invention.

BRIEF SUMMARY

Optical systems and methods of producing the same are provided. In an exemplary embodiment, the optical system includes a first anamorphic optic having a first focal length and a first focal line, where the first anamorphic optic is configured such that the first focal line is about parallel to a cross track direction. A second anamorphic optic has a second focal length and a second focal line, where the second focal length is different than the first first focal length. The second anamorphic optic is positioned such that the first focal line and the second focal line are in about the same location. The first and second anamorphic optics are aligned along an optical signal path, and are configured to provide afocal magnification of a signal beam along an along track direction to produce a magnified beam, where the along track direction is perpendicular to the cross track direction. A line scan imager includes an objective lens and a linear detector, and the second anamorphic optic is configured to direct the magnified beam at the objective lens.

An optical system is provided in another embodiment. The optical system includes a plurality of anamorphic optics including a first and second anamorphic optic. The plurality of anamorphic optics are configured to provide afocal magnification of a signal beam in an along track direction more than in a cross track direction to produce a magnified beam, where the along track and cross track directions are perpendicular. A line scan imager with an objective lens and a linear detector is configured such that the magnified beam impinges on the objective lens.

A method of scanning an item is provided in yet another embodiment. The method includes producing a signal beam from the item, and afocally magnifying the signal beam in an along track direction more than in a cross track direction to produce a magnified beam. The along track direction is perpendicular to the cross track direction. The magnified beam is directed into a line scan imager, where the line scan imager includes a linear detector positioned with a linear detector length aligned with the cross track direction and a linear detector width aligned with the along track direction.

BRIEF DESCRIPTION OF THE DRAWINGS

The present embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Figure 1:
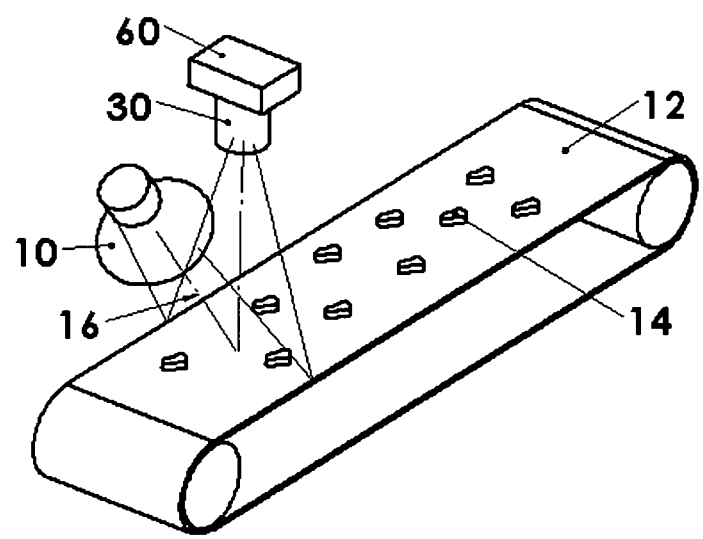
FIG. 1 illustrates an optical system and a line scan imager with a conveyor belt.

Reference is made to an exemplary embodiment in FIG. 1. A source 10 of illumination provides electromagnetic radiation, such as visible light, to illuminate at least a portion of a conveyor belt 12. Many different varieties of the source 10 may be used in various embodiments. For example, the source 10 may be a light bulb that provides electromagnetic radiation in the visible spectrum (light), and may also provide infrared and/or ultraviolet light. In alternate embodiments, the source 10 may be the sun such that ambient light is used, or the source 10 may provide monochromatic electromagnetic radiation, such as with a laser. The source 10 may provide other frequencies of electromagnetic radiation in alternate embodiments, such as X-rays, gamma rays, radio waves, microwaves, infrared radiation, ultraviolet radiation, and various combinations of frequencies. Certain frequencies of electromagnetic radiation may be more suitable in different uses. In this description, the electromagnetic radiation provided by the source 10 is generally referred to as "light," with the understanding that light from the visible spectrum is one exemplary embodiment and the source 10 may provide electromagnetic radiation in other or additional frequencies in alternate embodiments.

An optical system 30 and a line scan imager 60 are positioned to image the light from items 14 that are illuminated by the source 10. The conveyor belt 12 translates, and the source 10, optical system 30, and line scan imager 60 remain in a fixed position relative to the entire conveyor belt 12. As such, portions of the conveyor belt 12 pass in front of the source 10, the optical system 30, and the line scan imager 60 as the conveyor belt 12 translates. The optical system 30 is positioned to collect light from the source 10 as the light reflects or re-transmits from the conveyor belt 12 or from items 14 positioned on the conveyor belt 12. The line scan imager 60 is positioned to receive light from the optical system 30. The direction of movement of the conveyor belt 12 is referred to herein as the "along track" direction, and the "cross track" direction is perpendicular to the along track direction, so the cross track direction extends from one side or edge of the conveyor belt 12 to the opposite side or edge of the conveyor belt 12. The optical system 30 and line scan imager 60 may be used in embodiments that do not include a conveyor belt 12 in some embodiments, so the conveyor belt 12 is described herein as one exemplary use with the understanding that other uses are also possible. The item 14 sits on the conveyor belt 12 and moves with the translation of the conveyor belt 12, so the item 14 passes through an area illuminated by the source 10 such that light reflects, partially reflects, absorbs or is emitted from the item 14, to produce a signal beam 16.

Figure 2:
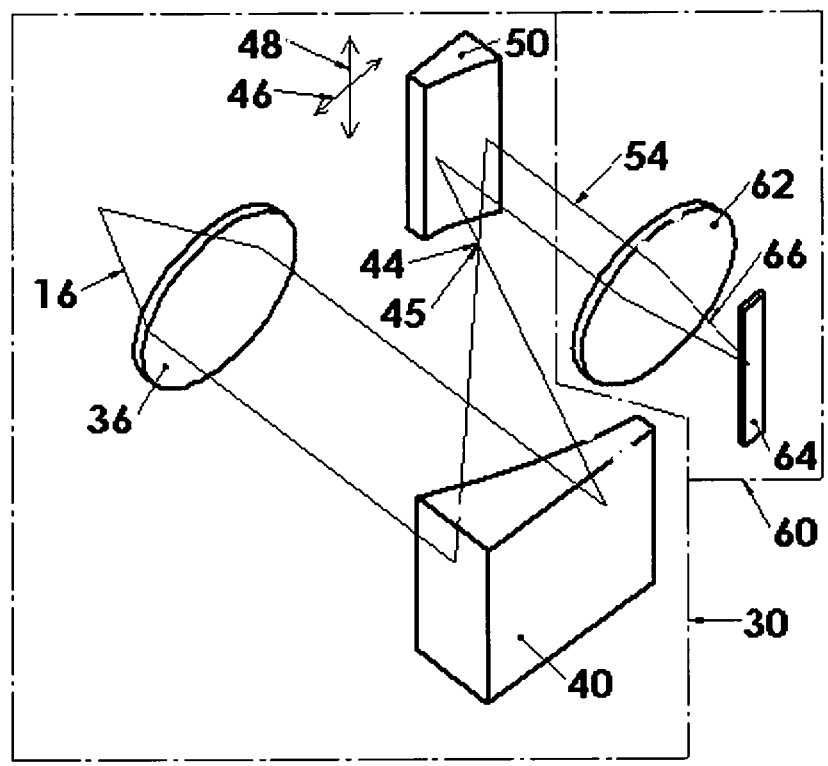
FIG. 2. is a perspective view of an exemplary optical system and line scan imager.

The signal from the surface of the conveyor belt 12 or the items 14 on the conveyor belt 12 (i.e. the signal beam 16) are illustrated in an exemplary embodiment in FIG. 2, where the signal beam 16 enters an optional collimating element 36. In alternate embodiments, the signal beam 16 may be collimated before entry into the optical system 30, in which case no collimating element 36 may be present. The signal beam 16 may be collimated or non-collimated in various embodiments, where a collimated beam is a beam in which all the rays of electromagnetic radiation are essentially parallel. A non-collimated beam includes rays of electromagnetic radiation that are not essentially parallel. Generally, if the signal beam 16 originates from an item 14 or object that is a large distance from the optical system 30 (i.e., a "far field"), the signal beam 16 will be collimated, and if the signal beam 16 originates from a close distance to the optical system 30 (i.e., a "near field"), the signal beam 16 will typically be non-collimated. In this description, a "large distance" between the origination point of the signal beam 16 and the optical system is about 10 meters or more, but other distances may be used in alternate embodiments. The collimating element 36 may be a rotationally symmetric element, such as a circularly symmetric lens (as illustrated), but the collimating element 36 may include a plurality of mirrors or other configurations in alternate embodiments. The collimating element 36 typically has equal optical powers in the X and Y directions, where the X and Y directions are perpendicular to the optical axis of the collimating optic and perpendicular to each other. However, in some embodiments the collimating element 36 may have asymmetric optical power, such that there is a greater or lesser degree of optical power in the X direction relative to the Y direction. Optical power is the degree to which an optic converges or diverges light.

In many embodiments, the signal beam 16 is collimated by the collimating element 36. However, in some embodiments it is possible for the signal beam 16 to pass through the collimating element 36 and remain or become non-collimated with diverging or converging rays of electromagnetic radiation, where the resulting rays diverge or converge at a known distribution. As such, subsequent components of the optical system 30 can be designed and configured for the known degree of divergence or convergence in the signal beam 16.

The signal beam 16 advances to a first anamorphic optic 40 that has a first focal length 42, where a first focal line 44 is positioned at the first focal length 42 from a surface of the first anamorphic optic 40. Thus, the term "focal length" for an anamorphic optic refers to the distance from the anamorphic optic where incoming collimated light will come to a line focus. For an anamorphic optic which is assigned a negative focal length, the focal length is the distance from the optic from where incoming collimated light will appear to have originated from as a line source. The first anamorphic optic 40 (and other optics described herein) may be a mirror, a lens, or other optical devices. The shape of the supporting material behind the optic surface may be modified as appropriate for supporting and positioning the optic surface. The first anamorphic optic 40 may be curved along one axis (referenced herein as the "curved axis 46") and essentially straight along another axis (referenced herein as the "straight axis 48"), similar to a surface of a cylinder. The straight axis 48 may not be perfectly straight in all embodiments, but the first anamorphic optic 40 is straighter along the straight axis 48 than along the curved axis 46. As such, the first anamorphic optic 40 provides asymmetric optical power, with a greater optical power along the curved axis 46 than along the straight axis 48.

The first anamorphic optic 40 is configured such that the straight axis 48 is effectively parallel to the cross-track direction of the belt, and the curved axis 46 is effectively parallel to the along-track direction of the belt, which is the same as the direction the belt is moving. The straight axis 48 may not literally be parallel to the cross-track direction because intervening optics (not illustrated) may change the direction of the signal beam 16, but the straight axis 48 is effectively parallel to the cross-track direction in that light from the cross-track direction impinges on the first anamorphic optic 40 as if it were parallel to the curved axis 46 (i.e. configured such that the straight axis 48 is effectively parallel to the cross-track direction.) As such, the signal beam 16 is focused into a first focal line 44 parallel to the cross-track direction at a distance from the first anamorphic optic 40 equal to the first focal length 42. Therefore, the signal beam 16 is focused at the first focal line 44 into a line, because the portions of the signal beam 16 along the straight axis 48 are generally transmitted similar to a planar mirror without a focal point 44.

In an exemplary embodiment, the first anamorphic optic 40 has a parabolic shape along the curved axis 46. In other words, the cross-sectional profile of the first anamorphic optic 40 may be a portion of a parabola. The parabolic profile nominally eliminates spherical aberration, which is an on-axis aberration that degrades performance. Furthermore, since there are minimal off-axis field angles along the straight axis 48, the parabolic shape substantially reduces or eliminates aberrations in the line image other than those stemming from manufacturing and alignment imperfections. Note that other shapes for the optical surface may be used in alternate embodiments, including but not limited to traditional cyclindrical mirrors, with a circular section as the curved surface of the mirror and acylindrical mirrors with non-circular surfaces along the curved surface.

In some embodiments, a lens (not illustrated) may be used for the first anamorphic optic 40. Such a lens has greater curvature along the curved axis than along the straight axis for at least one of its two surfaces, as described above for the mirror embodiment of first anamorphic optic 40, so the lens also provides asymmetrical optical power as described above. The lens may include at least two different optical materials to help reduce chromatic aberrations. The lens may have an acylindrical, circular, parabolic, or generalized conic profile along one dimension, and may have such a profile on one or more surfaces on the lens. Similar design considerations apply to optics, such as anamorphic prisms, other than mirrors or lenses.

The signal beam 16 impinges on a second anamorphic optic 50 after reflecting from the first anamorphic optic 40, where the second anamorphic optic 50 has a second focal length 52 such that the signal beam 16 is asymmetrically magnified. The first and second anamorphic optics 40, 50 are aligned along an optical signal path 56 such that they work in concert to provide approximate afocal magnification of the signal beam 16. An "approximately afocal optical system" is one with approximately no net convergence or divergence of the signal. That is, if a nearly collimated signal is input to an afocal system, the output beam is also nearly collimated, although the overall beam width may be changed if there is magnification. In an exemplary embodiment with mirrors for the first and second anamorphic optics 40, 50, the second focal length 52 may be less than the first focal length 42. The second anamorphic optic 50 also has a second focal line 45, where the second anamorphic optic 50 is configured such that the first and second focal lines 44, 45 are in about the same place. For example, the first and second focal lines 44, 45 may be within about 1 millimeter of each other for the entire length of the first and second focal lines 44, 45, or the first and second focal lines 44, 45 may be within about 0.5 percent of the first focal length from each other for the entire length of the first and second focal lines 44, 45. Configuring the first and second anamorphic optics 40, 50 such that the first and second focal lines 44, 45 are at about the same location leads to an image from the line scan imager 60 that is more in focus than if the first and second focal lines 44, 45 were at different locations. Alternative embodiments include anamorphic optical systems 30 with diverging optical elements, which are aligned to provide afocal magnification, and anamorphic prism pairs.

The second anamorphic optic 50 may be curved in the curved axis 46 and essentially straight in the straight axis 48, as described above for the first anamorphic optic 40. The second anamorphic optic 50 may also have a shape and optional coatings as described above for the first anamorphic optic 40. In an exemplary embodiment, The curved and straight axes 46, 48 for the first and second anamorphic optics 40, 50 may not be the same, but the straight axis 48 for the first anamorphic optic 40 is about parallel with the straight axis 48 for the second anamorphic optic 50. As such, the first and second anamorphic optics 40, 50 are both configured such that the curved surface and curved axis 46 are aligned to produce a line focus that is functionally parallel to the cross track direction. The first and second anamorphic optics 40, 50 are also positioned such that if light incident on the first anamorphic optic 40 is essentially collimated, that light will also be essentially collimated after being reflected from the second anamorphic optic 50.

In an exemplary embodiment with mirrors as the first and second anamorphic optics 40, 50, the first focal length 42 is greater than the second focal length 52, as mentioned above, so the first and second anamorphic optic 40, 50 magnify the signal beam 16 in the along track direction. Because of the magnification resulting from the different first and second focal lengths 42, 52 the beam reflected from the second anamorphic optic 50 is referred to herein as a magnified beam 54. The first and second anamorphic optics 40, 50 are less curved along the straight axis 48 than along the curved axis 46, which correspond to the cross track direction and the along track direction (as mentioned above), so the image is less magnified in the cross track direction than in the along track direction. Therefore, the first and second anamorphic optics 40, 50 produce an asymmetrically magnified image, where the image is magnified in the along track direction more so than in the cross track direction. In exemplary embodiments, the magnified beam is not magnified in the cross track direction, or is magnified by from about 1 times to about 1.5 times, or from about −0.5 times to about 1.5 times. Magnification in the cross track direction may produce distortion that is difficult to analyze, so embodiments with little to no cross track magnification generally require less signal processing for accurate analysis. However, the magnified beam 54 may be magnified from about 2 to about 50 times in the along track direction, or from about 2 to about 20 times in the along direction in different embodiments.

In alternate embodiments, the optical system 30 may include more than two anamorphic optics, as well as one or more planar mirrors, one or more lens, one or more filters, one or more diffraction elements, one or more anamorphic prisms or prism pairs, and other optical components.

The magnified beam 54 exits the optical system 30 and enters a line scan imager 60. The line scan imager 60 includes an objective lens 62 and a linear detector 64, and may include other components in alternate embodiments. The second anamorphic optic 50 (or another component of the optical system 30 that is downstream from the second anamorphic optic 50) is configured to direct the magnified beam 54 to the objective lens 62, and the objective lens 62 is configured to image the beam 66 onto the linear detector 64. The linear detector 64 has a linear detector length 68 that is greater than a linear detector width 70, where the linear detector length 68 is configured to align with the cross track direction and the linear detector width 70 is configured to align with the along track direction.

Figure 3:
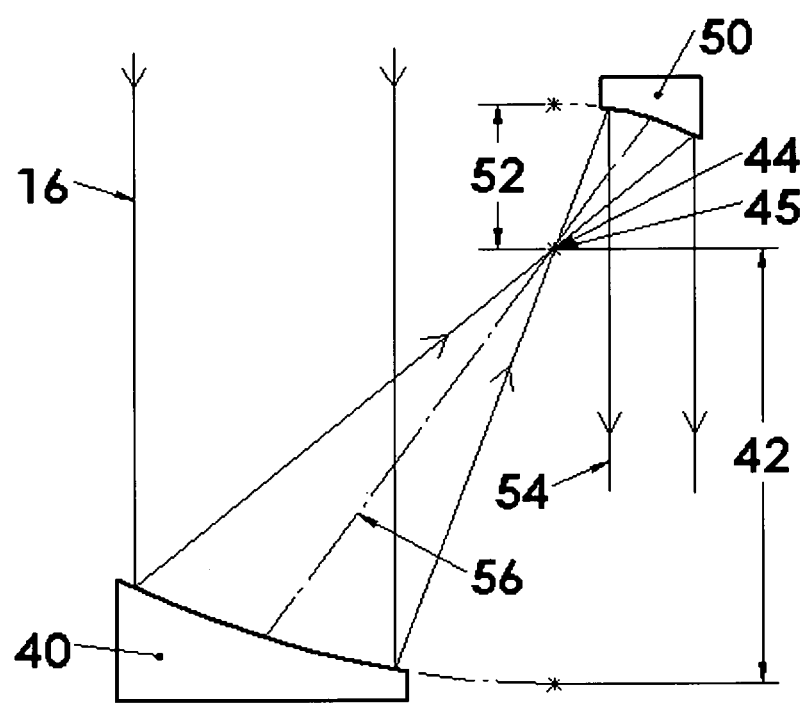
FIG. 3 illustrates a top view of an embodiment of an optical system.
Figure 4:
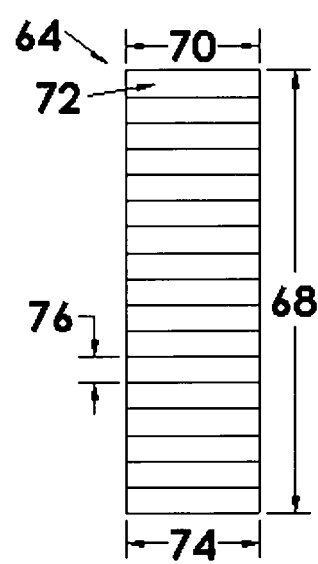
FIGS. 4 and 5 illustrate exemplary embodiments of a linear detector.

The linear detector 64 includes a plurality of sensing elements 72, as illustrated in FIG. 4, with continuing reference to FIGS. 1-3. Each sensing element 72 produces an electrical signal that indicates the magnitude of light (or other electromagnetic radiation) that impinges on the sensing element 72. Other factors that influence the electrical signal produced by the sensing element 72 include the time over which the signal is measured, commonly called the integration time, the sensor efficiency, which is typically a function of the light wavelength (or frequency), the bandwidth (i.e., the range of light wavelengths or frequencies) of the incoming signal, the area of the detector, and the solid angle of the incoming light (which is typically characterized by the f-number). The alignment of the linear detector length 68 with the cross track direction allows the linear detector to differentiate locations across the width (the cross track direction) of the conveyor belt 12 because different sensing elements 72 are associated with different locations across the width of the conveyor belt 12.

The asymmetrical magnification of the magnified beam 54 produces distortion, as mentioned previously, and this distortion can complicate analysis. In some embodiments, the sensing elements 72 in the linear detector 64 are asymmetric and this can compensate for the distortion. As such, a sensing element length 74 is greater than a sensing element width 76, where the sensing element length 74 is measured parallel to the linear detector width 70 and the sensing element width 76 is measured parallel with the linear detector length 68. The longer dimension of the sensing element length 74 (measured along the linear detector width 70) allows for more signal collection along the linear detector width 70, where the linear detector width 70 corresponds to the along track direction (and the curved axis 46), as described above. The greater signal collection along the sensing element length 74 may compensate for the distortion produced by the asymmetrical magnification of the magnified beam 54, such that the distortion is reduced or even eliminated. In an exemplary embodiment, the ratio of the sensing element width 76 to the sensing element length 74 is configured to reduce the distortion produced by the asymmetrical magnification of the magnified beam 54. In an exemplary embodiment with a perfect match, if the asymmetrical magnification is X, and the sensing element length is X times the sensing element width, there will be essentially no distortion, but the signal will be X times larger than embodiments (1) without asymmetric magnification of the signal beam and (2) with square sensing elements 72. In an alternate embodiment, the ratio of the magnification of the magnified beam 54 in the cross track direction compared to the magnification in the along track direction is within about 20 percent of the ratio of the sensing element width 76 to the sensing element length 74.

Figure 5:
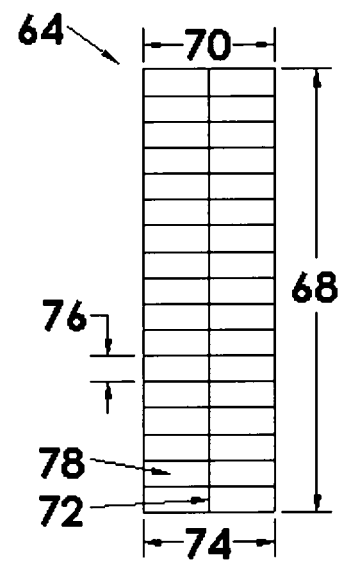

The linear detector 64 includes a plurality of sensing elements 72, as described above, where the sensing elements 72 produce an electrical signal associated with a position in time and space on the conveyor belt 12 (or other target of analysis). The sensing element 72 has a sensing element length 74 that is greater than a sensing element width 76, as described above, but the sensing element 72 may include more than one pixel 78 in some embodiments, as illustrated in FIG. 5 with continuing reference to FIGS. 1-4. In the embodiment illustrated in FIG. 5, each pixel 78 produces an electrical signal when light impinges on it, but the signals from the plurality of pixels 78 along the linear detector width 70 are combined to form a single signal for each sensing element 72. The embodiment of the linear detector 64 illustrated in FIG. 4 includes one pixel 78 per sensing element 72, and the embodiment illustrated in FIG. 5 includes two pixels 78 per sensing element 72.

The optical system 30 may be utilized with many different embodiments of the line scan imager 60. For example, the line scan imager 60 may be a hyperspectral line scan imager (not illustrated) that includes a slit and a diffraction element to separate the incoming beam (the magnified beam 54 in this description) into different frequencies. In this embodiment, the hyperspectral line scan imager includes a plurality of linear detectors combined to form a 2 dimensional array. One axis of the 2 dimensional array is associated with different positions along the cross track direction, and the other axis of the 2 dimensional array is associated with different frequencies of light (of other electromagnetic radiation) for one particular position on the conveyor belt 12. Other types of line scan imagers or other devices may also be used with the optical system 30 in alternate embodiments.

In an exemplary embodiment, the optical system 30 is combined with a hyperspectral line scan imager 60 and employed with a "waterfall" type sorter for a conveyor belt 12. In a "waterfall" sorter for a conveyor belt 12, items 14 are scanned as they fall off of the conveyor belt 12 so the items 14 can be scanned on two sides as they fall through free space. This can improve sorting accuracy for some types of items 14, but it requires very fast scan times to capture the signal beam 16 as the items 14 fall. Furthermore, a hyperspectral line scan imager 60 splits the signal beam 16 in a plurality of different frequencies. This improves analysis capabilities because different frequencies may include different information about an item 14, but it reduces the electrical signal from the sensing element 72 because the magnitude of light that impinges on sensing element 72 is reduced as the signal is split into many different frequency bands. As such, the signal beam 16 must be increased by about 2 to about 5 times its original strength to facilitate accurate sorting. A lower signal increase does not produce adequate signal strength and sorting accuracy is significantly diminished. Therefore, a hyperspectral line scan imager 60 with about 2 to about 5 times magnification in the along track direction can improve sorting because an item 14 can be viewed on more than a top side.

While at least one exemplary embodiment has been presented in the foregoing detailed description, it should be appreciated that a vast number of variations exist. It should also be appreciated that the exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:

1. An optical system comprising:
a first anamorphic optic having a first focal length and a first focal line, wherein the first anamorphic optic is configured such that the first focal line is about parallel to a cross track direction;
a second anamorphic optic having a second focal length and a second focal line, wherein the second focal length is different than the first focal length, wherein the second anamorphic optic is positioned such that the first focal line and the second focal line are in about the same location, wherein the first and second anamorphic optics are aligned along an optical signal path, and wherein the first and second anamorphic optics are configured to provide afocal magnification to a signal beam along an along track direction to produce a magnified beam, wherein the along track direction is perpendicular to the cross track direction; and
a line scan imager, wherein the line scan imager comprises an objective lens and a linear detector, wherein the second anamorphic optic is configured to direct the magnified beam at the objective lens, wherein the linear detector has a linear detector length and a linear detector width, and wherein the linear detector length is greater than the linear detector width.

2. The optical system of claim 1 wherein the line scan imager is a hyperspectral line scan imager.

3. The optical system of claim 1 wherein the linear detector comprises a plurality of linear detectors.

4. The optical system of claim 1 wherein the first anamorphic optic and the second anamorphic optic are positioned such that the magnified beam is magnified in the along track direction more than in the cross track direction.

5. The optical system of claim 4 wherein the first anamorphic optic and the second anamorphic optic are configured such that the magnified beam is magnified from about 2 times to about 50 times in the along track direction.

6. The optical system of claim 4 wherein the first anamorphic optic and the second anamorphic optic are configured such that the magnified beam is magnified from about 2 times to about 20 times in the along track direction and from about −0.5 times to about 1.5 times in the cross track direction.

7. The optical system of claim 1 wherein the linear detector is positioned such that the linear detector length is aligned with the cross track direction and the linear detector width is aligned with the along track direction.

8. The optical system of claim 7 wherein the linear detector comprises a plurality of sensing elements, wherein each of the plurality of sensing elements comprises a sensing element length and a sensing element width, wherein the sensing element length is measured parallel to the linear detector width and the sensing element width is measured parallel to the linear detector length, and wherein the sensing element length is greater than the sensing element width.

9. The optical system of claim 8 wherein each of the plurality of sensing elements comprise a plurality of pixels aligned about parallel to the along track direction.

10. The optical system of claim 8 wherein a ratio of the sensing element width to the sensing element length is configured to reduce distortion in the magnified beam by about 50 percent or more.

11. The optical system of claim 1 further comprising a collimating element, wherein the collimating element is configured to collimate the signal beam, and wherein the collimating element and the first anamorphic optic are configured such that the collimated signal beam contacts the first anamorphic optic.

12. An optical system comprising:
a plurality of anamorphic optics comprising a first anamorphic optic and a second anamorphic optic, where the plurality of anamorphic optics are configured to provide afocal magnification to a signal beam in an along track direction more than in a cross track direction to produce a magnified beam, wherein the along track direction is perpendicular to the cross track direction, and;
a line scan imager, wherein the line scan imager comprises an objective lens and a linear detector, wherein the line scan imager is configured such that the magnified beam impinges on the objective lens, wherein the linear detector comprises a linear detector length and a linear detector width, and wherein the linear detector length is greater than the linear detector width.

13. The optical system of claim 12 wherein the linear detector comprises a plurality of sensing elements, wherein the plurality of sensing elements comprise a sensing element width and a sensing element length that is longer than the sensing element width.

14. The optical system of claim 13 wherein the sensing element length is configured to align with the along track direction and the sensing element width is configured to align with the cross track direction.

15. The optical system of claim 13 wherein each of the plurality of sensing elements comprises one pixel aligned about parallel to the along track direction.

16. The optical system of claim 12 wherein the linear detector length is aligned with the cross track direction and the linear detector width is aligned with the along track direction.

17. A method of scanning an item comprising:
producing a signal beam from the item;
providing afocal magnification to the signal beam in an along track direction more than in a cross track direction to produce a magnified beam, wherein the along track direction is perpendicular to the cross track direction; and directing the magnified beam into a line scan imager, wherein the line scan imager comprises a linear detector that is positioned with a linear detector length aligned with the cross track direction and a linear detector width aligned with the along track direction, and wherein the linear detector length is greater than the linear detector width.

18. The method of claim 17 wherein directing the magnified beam comprises directing the magnified beam into the line scan imager wherein the linear detector comprises a plurality of sensing elements, wherein the plurality of sensing elements have a sensing element width measured parallel to the linear detector length and a sensing element length measured parallel to the linear detector width, and the sensing element length is greater than the sensing element width.

19. The method of claim 18 wherein directing the magnified beam comprises directing the magnified beam into the line scan imager wherein each of the plurality of sensing elements comprise a plurality of pixels aligned approximately parallel to the along track direction.

20. The method of claim 17 further comprising:
reducing distortion in the magnified beam by providing a plurality of sensing elements in the linear detector, wherein the plurality of sensing elements are asymmetric.

* * * * *